(12) United States Patent
Gouko et al.

(10) Patent No.: US 10,054,437 B2
(45) Date of Patent: *Aug. 21, 2018

(54) ABNORMALITY ESTIMATION APPARATUS HAVING A HEAT FLOW SENSOR THAT DETECTS A HEAT FLOW CAUSED BY AN ELASTIC DEFORMATION OF AN ELASTIC BODY

(71) Applicant: DENSO CORPORATION, Kariya, Aichi-pref. (JP)

(72) Inventors: Norio Gouko, Kariya (JP); Toshihisa Taniguchi, Kariya (JP); Atusi Sakaida, Kariya (JP); Keiji Okamoto, Kariya (JP); Yoshihiko Shiraishi, Kariya (JP); Masahiro Asano, Kariya (JP)

(73) Assignee: DENSO CORPORATION, Kariya, Aichi-pref. (JP)

( * ) Notice: Subject to any disclaimer, the term of this patent is extended or adjusted under 35 U.S.C. 154(b) by 0 days.

This patent is subject to a terminal disclaimer.

(21) Appl. No.: 15/484,231

(22) Filed: Apr. 11, 2017

(65) Prior Publication Data

US 2017/0299383 A1    Oct. 19, 2017

(30) Foreign Application Priority Data

Apr. 14, 2016 (JP) .................................. 2016-081187

(51) Int. Cl.
*G01B 21/32* (2006.01)
*G01N 25/20* (2006.01)
*B65G 43/00* (2006.01)

(52) U.S. Cl.
CPC .............. *G01B 21/32* (2013.01); *B65G 43/00* (2013.01); *G01N 25/20* (2013.01)

(58) Field of Classification Search
CPC ........... G01L 5/06; G01L 5/226; G01K 17/00; G01N 25/00; G01N 25/20; G01B 21/32;
(Continued)

(56) References Cited

U.S. PATENT DOCUMENTS 4,674,310 A * 6/1987 Ginzburg ................ B21B 38/02
72/11.4
5,123,284 A * 6/1992 Edinburgh ................ G01L 5/10
73/159

(Continued)

FOREIGN PATENT DOCUMENTS

JP    H09-133592 A    5/1997

*Primary Examiner* — Harshad R Patel
*Assistant Examiner* — Brandi Hopkins
(74) *Attorney, Agent, or Firm* — Harness, Dickey & Pierce, P.L.C.

(57) ABSTRACT

An abnormality estimation apparatus for estimating an abnormality in a belt of a belt conveyor includes a displacement part that is displaced in accordance with tension or a change of the tension of the belt when the displacement part is caused to abut against the belt to receive the tension of the belt, an elastic body that is elastically deformed in accordance with displacement of the displacement part, a heat flow sensor that detects a heat flow occurring due to elastic deformation of the elastic body, and an abnormality estimation part that estimates whether there is an abnormality in the belt based on a detection result by the heat flow sensor.

5 Claims, 9 Drawing Sheets (58) Field of Classification Search
CPC ................ B65G 43/00; G03G 15/206; G03G 2215/2009
See application file for complete search history.

(56) References Cited

U.S. PATENT DOCUMENTS

| | | | | |
|---|---|---|---|---|
| 5,666,998 A | * | 9/1997 | De Jager | B65H 59/40 139/194 |
| 2008/0250872 A1 | * | 10/2008 | Lamprillo | B65H 59/40 73/862.41 |
| 2008/0307885 A1 | * | 12/2008 | Ravitch | G01H 5/00 73/597 |

* cited by examiner

FEED DIRECTION OF BELT

FIG.9

FEED DIRECTION OF BELT

ABNORMALITY ESTIMATION APPARATUS HAVING A HEAT FLOW SENSOR THAT DETECTS A HEAT FLOW CAUSED BY AN ELASTIC DEFORMATION OF AN ELASTIC BODY

This application claims priority to Japanese Patent Application No. 2016-81187 filed on Apr. 14, 2016, the entire contents of which are hereby incorporated by reference.

BACKGROUND OF THE INVENTION

1. Field of the Invention

The present invention relates to an abnormality estimation apparatus for estimating abnormality in a belt of a belt conveyer.

2. Description of Related Art

In a belt conveyer apparatus for conveying hauls, if a belt of a belt conveyer is broken during its operation, the operation of the whole apparatus is stopped. Accordingly, it is important to periodically check the state of the belt (load, age deterioration, use period and so on).

Japanese Patent Application Laid-open No. H9-133592 describes a life prediction apparatus for predicting a life of a belt. In this life prediction apparatus, a frictional slide workload is calculated as a parameter related to friction between the belt and a gear that rotates the belt based on geometric data, material data and external force data. The geometric data includes the diameter and center position of the gear, and dimensions of the teeth of the gear and the belt. The material data includes the elastic modulus, and coefficient of friction of the belt. The external force data includes a predetermined load torque. The life of the belt is predicted by referring to a preset S-N curve showing a relationship between the frictional slide workload and the durable life of the belt.

However, the life prediction apparatus described in the above patent document has a problem in that it is not possible to predict the life of the belt with a sufficiently high degree of accuracy, because it does not check the actual state of the belt while the belt conveyer is in operation.

It is known to use a load cell which converts a load into an electric signal for measuring the actual state of a belt of a belt conveyer. Such a load cell is installed such that its sensing part including a sensor is in direct contact with a belt so that the sensing part directly receives the tension of the belt. Accordingly, there is a concern that the sensor may be damaged by the tension of the belt.

SUMMARY

An exemplary embodiment provides an abnormality estimation apparatus for estimating an abnormality in a belt of a belt conveyor, including:

a displacement part that is displaced in accordance with tension or a change of the tension of the belt when the displacement part is caused to abut against the belt to receive the tension of the belt;

an elastic body that is elastically deformed in accordance with displacement of the displacement part;

a heat flow sensor that detects a heat flow occurring due to elastic deformation of the elastic body; and an abnormality estimation part that estimates whether there is an abnormality in the belt based on a detection result by the heat flow sensor.

According to the exemplary embodiment, there is provided an abnormality estimation apparatus having a tension sensor which is not damaged easily, and being capable of estimating whether there is an abnormality in a belt of a belt conveyor even while the belt conveyor is in operation.

Other advantages and features of the invention will become apparent from the following description including the drawings and claims.

PREFERRED EMBODIMENTS OF THE INVENTION

First Embodiment

Figure 1:
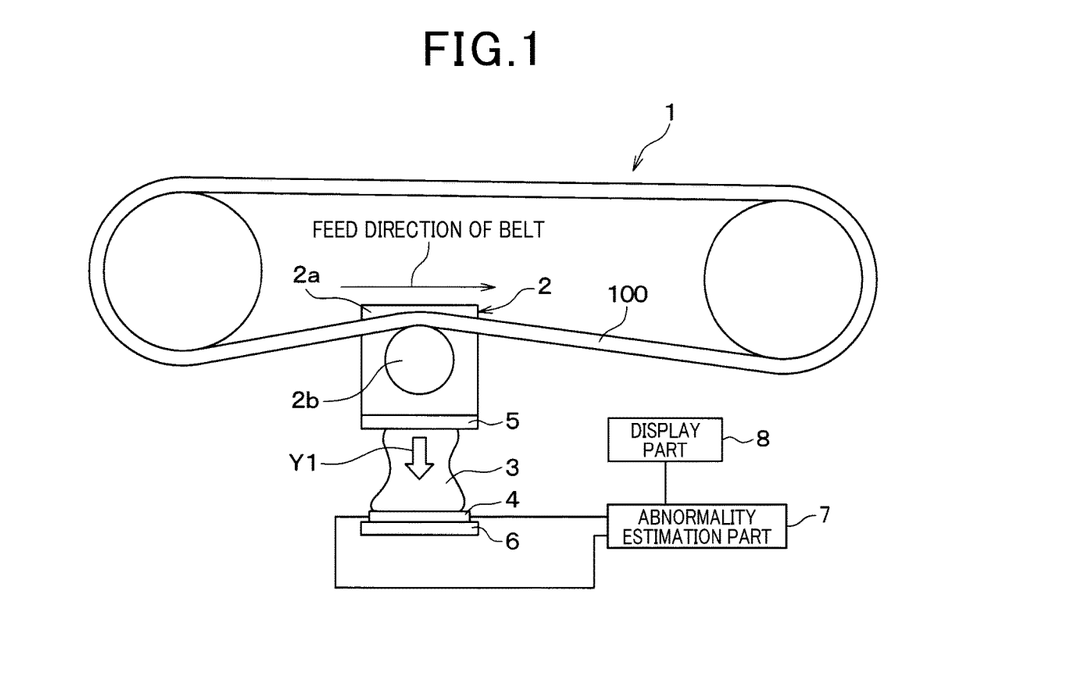
FIG. 1 is a diagram showing the overall structure of a belt conveyor provided with an abnormality estimation apparatus according to a first embodiment of the invention.
Figure 2:
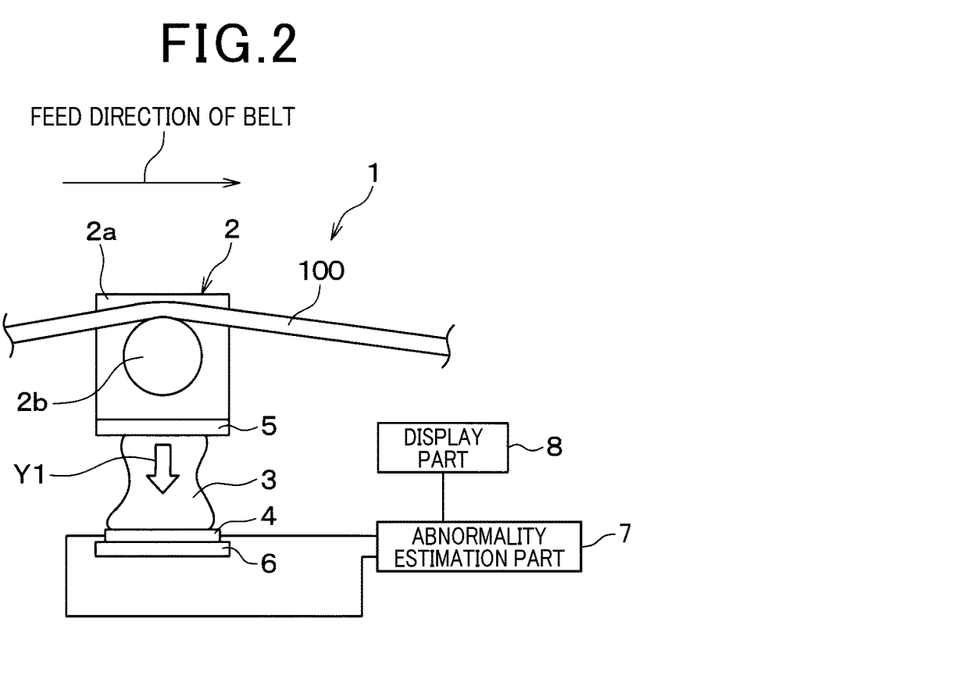
FIG. 2 is a diagram showing the structure of an abnormality estimation apparatus according to the first embodiment of the invention.
Figure 3:
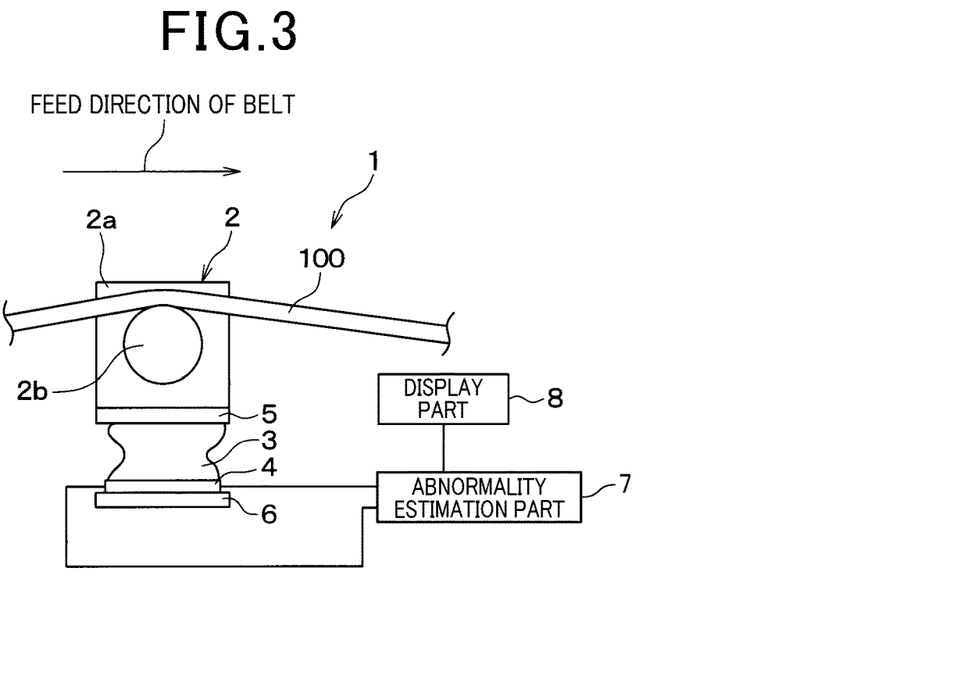
FIG. 3 is another diagram showing the structure of the abnormality estimation apparatus according to the first embodiment of the invention.

An abnormality estimation apparatus 1 according to a first embodiment of the invention is described with reference to FIGS. 1 to 6. The abnormality estimation apparatus 1 is an apparatus for estimating an abnormality in a belt 100 of a belt conveyor show in FIG. 1. FIG. 2 is a diagram showing the structure of the abnormality estimation apparatus 1 when the tension of the belt 100 starts to be measured. FIG. 3 is a diagram showing the structure of the abnormality estimation apparatus 1 when the tension of the belt 100 has increased thereafter. The abnormality estimation apparatus 1 includes a displacement part 2, an elastic body 3, a heat flow sensor 4, plate-like members 5 and 6, an abnormality estimation part 7 and a display part 8. The arrow Y1 in FIG. 2 shows the direction of displacement of the elastic body 3 at a time when the tension of the belt 100 has increased.

As shown in FIGS. 2 and 3, the plate-like member 6, the heat flow sensor 4, the elastic body 3, the plate-like member 5 and the displacement part 2 are stacked in this order from the downward side.

The displacement part 2 includes a portion which is caused to abut against the belt 100 to receive the tension of the belt 100. The displacement part 2 is displaced in accordance with the tension or a change of the tension of the belt 100 when the portion of the displacement part 2 is caused to abut against the belt 100. As shown in FIGS. 2 and 3, the displacement part 2 includes a proximal portion 2a and a roller portion 2b.

The proximal portion 2a of the displacement part 2 directly or indirectly connects with the elastic part 3 to apply a pressing force to the elastic part 3 in accordance with the tension of the belt 100. In this embodiment, as shown in FIGS. 2 and 3, the proximal portion 2a of the displacement part 2 is formed in a roughly cubic shape, and connects with the elastic body 3 through the plate-like member 5. The proximal portion 2a of the displacement part 2 is made of stainless steel, for example. The plate-like member 5 is made of stainless steel, for example.

The roller portion 2b is a cylindrical rotating body rotatably supported by the proximal portion 2a. The roller portion 2b rotates when it is caused to abut against the belt 100 to feed the belt 100 in the feed direction shown by the arrow in FIGS. 2 and 3. The roller portion 2b is made of Delrin resin, for example.

The proximal portion 2a and the roller portion 2b are displaced in accordance with the tension of the belt 100. Specifically, the proximal portion 2a is displaced together with the roller portion 2b in the direction perpendicular to the feed direction when the roller portion 2b receives the tension of the belt 100. As a result of the displacement of the proximal portion 2a, the elastic body 3 is pressed by the plate-like member 5 and is deformed accordingly.

The elastic body 3 is deformed in accordance with the displacement of the displacement part 2 caused by the tension or a change of the tension of the belt 100. The elastic body 3 is made of urethane rubber, for example. The elastic modulus of the material of the elastic body 3 is smaller than that of the displacement part 2 in this embodiment. However, the elastic modulus of the material of the elastic body 3 may be larger than that of the displacement part 2.

The heat flow sensor 4 is a sensor for detecting a heat flow caused by an elastic deformation of the elastic body 3. The heat flow sensor 4 is disposed at a position where a heat flow caused by an elastic deformation of the elastic body 3 can be detected. In this embodiment, the heat flow sensor 4 is disposed so as to be in contact with the elastic body 3. The heat flow sensor 4 outputs a sensor signal depending on a heat flow directing from the inside to the outside of the elastic body 3.

Figure 4:
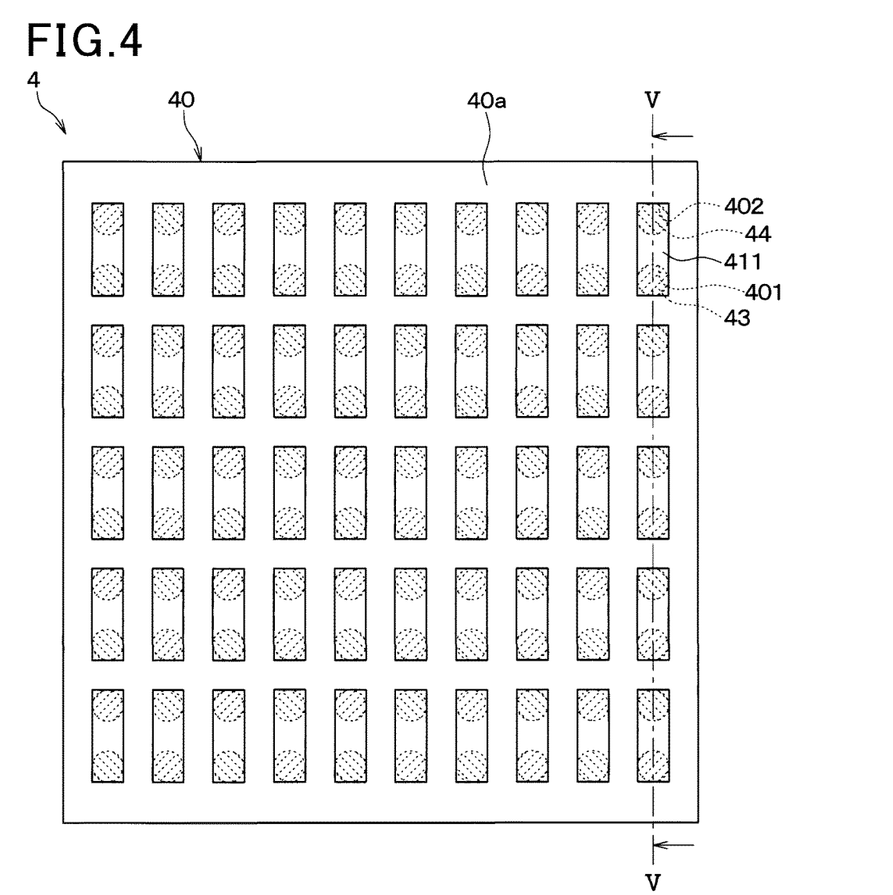
FIG. 4 is a plan view of a heat flow sensor included in the abnormality estimation apparatus according to the first embodiment of the invention.
Figure 5:
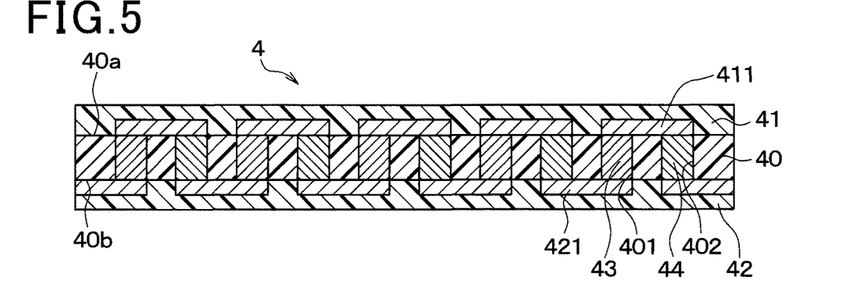
FIG. 5 is a cross-sectional view of FIG. 4 taken along line V-V.

As shown in FIGS. 4 and 5, the heat flow sensor 4 has a structure in which an insulating substrate 40, a front surface protecting member 41 and a back surface protecting member 42 are integrated such that first inter-layer connecting members 43 and second inter-layer connecting members 44 are connected in series alternately therein. In FIG. 4, the front surface protecting member 41 is omitted from illustration. Each of the insulating substrate 40, the front surface protecting member 41 and the back surface protecting member 42 is made of resin material having flexibility (thermoplastic resin, for example) formed in a film shape. The insulating substrate 40 is formed with first via holes 401 and second via holes 402 which penetrate through in the thickness direction. Each of the first via holes 401 is filled with a first inter-layer connecting member 43 made of thermoelectric material (metal or semiconductor, for example). Each of the second via holes 402 is filled with a second inter-layer connecting member 44 made of thermoelectric material (metal or semiconductor, for example), which is different from the first inter-layer connecting member 43. A front surface conductor pattern 411 is disposed on the front surface 40a of the insulating substrate 40. The front surface conductor pattern 411 makes a connecting part that connects one end of the first inter-layer connecting member 43 to one end of the second inter-layer connecting member 44. A back surface conductor pattern 421 is disposed on the back surface 40b of the insulating substrate 40. The back surface conductor pattern 421 makes a connecting part that connects the other end of the first inter-layer connecting member 43 to the other end of the second inter-layer connecting member 44. In the following, the side on the one end of the first or second inter-layer connecting member 43 or 44, that is, the side on the front surface protecting member 41 is referred to as the front side of the heat flow sensor 4. Likewise, the side on the other end of the first or second inter-layer connecting member 43 or 44, that is, the side on the back surface protecting member 42 is referred to as the back side of the heat flow sensor 4.

As shown in FIGS. 2 and 3, the heat flow sensor 4 having the above described structure is disposed such that the elastic body 3 is located on the front side of the heat flow sensor 4. The heat flow sensor 4 is fixed to the other ends of the first and second inter-layer connecting member 43 and 44, that is, to the plate-like member 6 disposed on the side of the back surface protecting member 42.

When a heat flow passes the heat flow sensor 4 in the thickness direction of the heat flow sensor 4, a difference in temperature occurs between the front side and the back side of the heat flow sensor 4. More specifically, when a heat flow passes the heat flow sensor 4 in the thickness direction of the heat flow sensor 4, a difference in temperature occurs between the connecting parts on the side of the one ends of the first and second inter-layer connecting members 43 and 44 and the connecting parts on the side of the other ends of the first and second inter-layer connecting members 43 and 44. As a result, an electromotive force occurs in the first and second inter-layer connecting members 43 and 44 due to the Seebeck effect. The heat flow sensor 4 outputs, as a sensor signal (a voltage signal, for example) the electromotive force depending on the heat flow passing between the front side and the back side of the heat flow sensor 4. In this embodiment, the heat flow sensor 4 is configured to generate a positive electromotive force when a heat flow passes from the front side to the back side of the heat flow sensor 4.

The elastic body 3 generates heat therein when the elastic body 3 is compressed or expanded, and generates cold therein when the elastic body 3 returns from a state of being applied with an external force from outside to be compressed to the initial state. There is a correlation between the magnitude of the absolute value of an electromotive force generated by the heat flow sensor 4 and a deformation of the elastic body 3 (the amount or variation of a deformation of the elastic body 3, for example). Generally, as the deformation amount of the elastic body 3 increases, a heat flux caused by the deformation of the elastic body 3 increases and the temperature difference between the front side and the back side of the heat flow sensor 4 increases. Accordingly, as the deformation amount of the elastic body 3 increases, the temperature difference between the connecting parts on the side of the one ends of the first and second inter-layer connecting members 43 and 44 and the connecting parts on the side of the other ends of the first and second inter-layer connecting members 43 and 44 increases, as a result of which the absolute value of the electromotive force generated by the heat flow sensor 4 increases.

Since the heat flow sensor 4 has the above described structure, it can be disposed on various surfaces which are not flat (curved surfaces, for example). In addition, since the thickness of the heat flow sensor 4 can be made small while ensuring a sufficiently large electromotive force to be generated, it is possible to reduce a detection error by reducing the thermal resistance in the heat flow sensor 4 by reducing the thickness of the heat flow sensor 4.

The abnormality estimation part 7 calculates the tension or a change of the tension of the belt 100 based on the heat flow due to the elastic deformation of the elastic body 3 detected by the heat flow sensor 4, and estimates an abnormality in the belt 100 based on the calculated tension or a change of the tension. The abnormality estimation part 7 is an electronic control unit comprised of a microcomputer, a memory as a storage device, and peripheral circuits. The memory stores data representing a relationship between the tension of the belt 100 and the electromotive force to be generated by the heat flow sensor 4 when the plate-like member 6 is placed at a predetermined position. Further, the memory stores data representing a relationship between a change of the tension of the belt 100 and the electromotive force generated by the heat flow sensor 4. The memory is a non-transitory storage medium.

Specifically, the abnormality estimation part 7 calculates the tension or a change of the tension of the belt 100 based on the sensor signal outputted from the heat flow sensor 4, that is, based on the electromotive force generated in the heat flow sensor 4, and performs a load estimation to estimate the load of the belt 100 from the tension or a change of the tension of the belt 100. For example, if the tension of the belt 100 exceeds a predetermined value within a predetermined time period, the abnormality estimation part 7 estimates that an extremely heavy haul has been placed on the belt 100, or that the conveyance by the belt 100 has been stopped. On the other hand, if the tension of the belt 100 falls below a predetermined value within a predetermined time period, the abnormality estimation part 7 estimates that belt 100 has been worn down and elongated.

Further, the abnormality estimation part 7 performs a life diagnosis to predict a time when the belt 100 will be broken based on the load (tension) of the belt 100. For example, the abnormality estimation part 7 predicts a time when the belt 100 will be broken based on the number of times that the belt 100 was applied with a load larger than a predetermined value within a predetermine time period (within one day, for example).

Also, the abnormality estimation part 7 controls the operation of the display part 8 by performing a calculation process in accordance with programs stored in the memory. For example, the abnormality estimation part 7 causes the display part 8 to display results of the abnormality diagnosis.

Next, the operation of the abnormality estimation apparatus 1 according to this embodiment is explained.

As shown in FIG. 2, the plate-like member 6 of the abnormality estimation apparatus 1 is placed at the predetermined position such that the belt 100 is abutted against the displacement part 2 of the abnormality estimation apparatus 1. At this time, the displacement part 2 displaces in accordance with the position of the displacement part 2 and the tension or a change of the tension of the belt 100, causing the elastic body 3 to be compressed to a certain extent.

When the elastic body 3 is compressed as above, the molecules inside the elastic body 3 are aligned, as a result of which heat is generated inside the elastic body 3. Accordingly, a heat flow heading from the inside of the elastic body 3 to the outside occurs. Since this heat flow passes the front side of the heat flow sensor 4, there occurs a temperature difference between the front side and the back side of the heat flow sensor 4. As a result, an electromotive force occurs as the sensor signal corresponding to the tension of the belt 100, and the abnormality estimation part 7 calculates the tension of the belt 100 based on the sensor signal. Specifically, to calculate the tension of the belt 100, the abnormality estimation part 7 reads the data representing the relationship between the tension of the belt 100 and the electromotive force generated by the heat flow sensor 4 from the memory. The tension of the belt 100 calculated by abnormality estimation part 7 at this time is stored in the memory as an initial tension at the time of start of measurement. Incidentally, the heat flux caused by compressing the elastic body 3 at the time of start of measurement is small and released to the outside with the passage of time, and becomes as small as undetectable after an elapse of a predetermined time.

In a case where the tension of the belt 100 increases after the start of measurement, the displacement part 2 is displaced downward in FIG. 3, and as a result the elastic body 3 is compressed more then than at the start of measurement. In this case, there occurs an electromotive force in accordance with the degree of a change of the tension of the belt 100. The abnormality estimation part 7 calculates the tension of the belt 100 at this moment that has increased. The abnormality estimation part 7 calculates the tension of the belt 100 at this moment that has increased from the initial tension as a second stage tension. If the tension of the belt 100 increases beyond a predetermined value, the belt 100 becomes roughly linear in shape.

In a case where the tension of the belt 100 decreases after the start of measurement or after being compressed more after the start of measurement, the displacement part 2 is displaced upward in FIG. 3 to return to the initial state. In this case, the compression of the elastic body 3 is released and the elastic body 3 restores from the elastic deformation, as a result of which cold occurs inside the elastic body 3. As a result, since the temperature of the front side of the heat flow sensor 4 decreases, the temperature difference between the front side and the back side of the heat flow sensor 4 changes from that at the start of measurement. Accordingly, there occurs a change in the electromotive force generated by the feat flow sensor 4. The abnormality estimation part 7 calculates the tension of the belt 100 at this moment that has decreased. The abnormality estimation part 7 calculates the tension of the belt 100 at this moment that has decreased from the initial tension or the second stage tension. When the sign of the temperature difference between the front side and the back side of the heat flow sensor 4 changes after the tension of the belt 100 decreases, also the sign of the electromotive force changes. The abnormality estimation part 7 performs the abnormality diagnosis for the belt 100 as above based on the tension or a change of the tension of the belt 100, and causes the display part 8 to display a diagnostic result.

In the abnormality estimation apparatus 1, the displacement part 2 is displaced in accordance with the tension or a change of the tension of the belt 100, and the elastic body 3 is deformed in accordance with the displacement of the displacement part 2. According to the abnormality estimation apparatus 1, it is possible to measure the tension or a change of the tension of the belt 100 by detecting a change of the heat flow caused by an elastic deformation of the elastic body 3 by the heat flow sensor 4, and perform the abnormality diagnosis for the belt 100 as described above based on the tension or a change of the tension of the belt 100 detected. As described above, the abnormality estimation apparatus 1 is configured such that the tension of the belt 100 is not directly received by the heat flow sensor 4, but the elastic body 3 is caused to abut against the heat flow sensor 4. Therefore, according to the tension measuring apparatus 1, it is possible to prevent the problem in the conventional art which uses a load cell, i.e. that a sensor may be easily damaged.

Further, according to the abnormality estimation apparatus 1, it is possible to measure the tension or a change of the tension of the belt 100 and perform the abnormality diagnosis even while the belt conveyor is in operation and the belt 100 is being fed. Further, according to the abnormality estimation apparatus 1, it is possible to measure the tension or a change of the tension of the belt 100 and perform the abnormality diagnosis when the belt conveyor is out of operation and the belt 100 is stationary.

Figure 6:
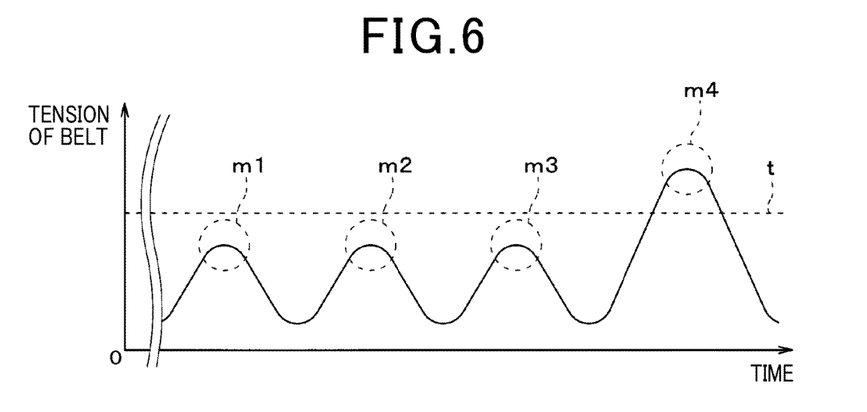
FIG. 6 is a diagram showing an example of transition with time of the tension of the belt when the abnormality estimation apparatus is in operation.

FIG. 6 is a diagram showing an example of transition with time of the tension of the belt 100, in which the horizontal axis represents time, the vertical axis represents the tension, and m1 to m6 represent local maximums of the tension of the belt 100. In this example, the tension of the belt 100 increases within a predetermined time period in accordance with weights of haul conveyed on the belt 100. The broken line t in FIG. 6 represents a threshold border between normal and abnormal states of the belt 100. In the example of FIG. 6, at the time when the local maximum m4 exceeds the threshold border t, it is estimated that the belt 100 is in an abnormal state because of an extremely heavy haul being placed on the belt 100, for example. This state is indicated on the display part 8.

As described above, the abnormality estimation apparatus 1 is configured such that the tension of the belt 100 is not directly received by the heat flow sensor 4, but the elastic body 3 is caused to abut against the heat flow sensor 4. Therefore, according to the abnormality estimation apparatus 1, it is possible to prevent the problem in the conventional art which uses a load cell, a sensor of which may be easily damaged. Further, according to the abnormality estimation apparatus 1, it is possible to measure the tension of the belt 100 and perform the abnormality diagnosis even while the belt conveyor is in operation.

As described above, the abnormality estimation apparatus 1 includes the displacement part 2 which is displaced in accordance with the tension or a change of the tension of the belt 100 when it is caused to abut against the belt 100 to receive the tension of the belt 100, the elastic body 3 which is elastically deformed in accordance with the displacement of the displacement part 2, the heat flow sensor 4 which detects a heat flow caused by the elastic deformation of the elastic body 3, and the abnormality estimation part 7 which estimates an abnormality in the belt 100 based on detection results of the heat flow sensor 4.

In the abnormality estimation apparatus 1, the displacement part 2 is displaced in accordance with the tension or a change of the belt 100, and the elastic body 3 is deformed in accordance with the deformation of the displacement part 2. According to the abnormality estimation apparatus 1, it is possible to detect a change of a heat flow caused by a deformation of the elastic body 3 to measure the tension or a change of the tension of the belt 100, and performs the abnormality diagnosis for the belt 100 based on the tension or a change of the tension detected. As described above, the abnormality estimation apparatus 1 is configured such that the tension of the belt 100 is not directly received by the heat flow sensor 4, but the elastic body 3 is caused to abut against the heat flow sensor 4. Therefore, according to the abnormality estimation apparatus 1, it is possible to prevent the problem in the conventional art which uses a load cell having a sensor that may be easily damaged.

In the abnormality estimation apparatus 1, the displacement part 2 includes the roller portion 2b which rotates when caused to abut against the belt 100 to feed the belt 100.

Accordingly, the abnormality estimation apparatus 1 can displace the displacement part 2 to measure the tension of the belt 100 while feeding the belt 100 smoothly using the roller portion 2b.

Second Embodiment

Figure 7:
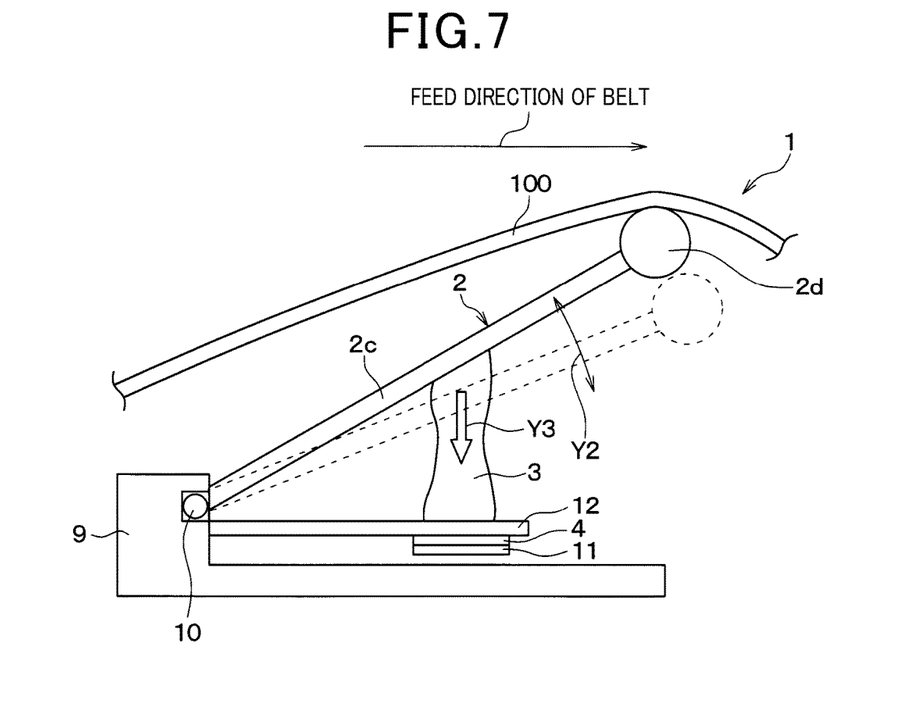
FIG. 7 is a diagram showing the structure of an abnormality estimation apparatus according to a second embodiment of the invention.
Figure 8:
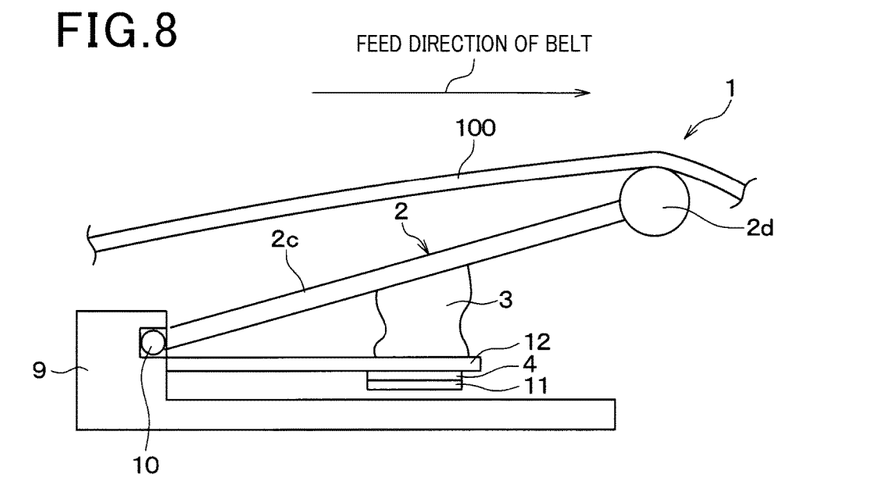
FIG. 8 is another diagram showing the structure of the abnormality estimation apparatus according to the second embodiment of the invention.

Next a second embodiment of the invention is described with a focus on differences with the first embodiment referring to FIGS. 7 and 8.

In FIGS. 7 and 8, the abnormality estimation part 7 and the display part 8 are omitted from illustration. In FIG. 7, the arrow Y2 shows the direction of displacement of the displacement part 2 at a time when the tension of the belt 100 has changed, and the arrow Y3 in FIG. 7 shows the direction of displacement of the elastic body 3 at a time when the tension of the belt 100 has increased.

The abnormality estimation apparatus 1 of this embodiment includes, in addition to the displacement part 2, the elastic body 3, the heat flow sensor 4, the abnormality estimation part 7 and the display part 8, a case part 9 for supporting the elastic body 3, a support mechanism 10 which causes the case part 9 to support the displacement part 2, a radiator 11, and a plate-like member 12.

In this embodiment, the displacement part 2 rotates with the support mechanism 10 as a fulcrum in accordance with the tension or a change of the tension of the belt 100 at a time when the displacement part 2 is caused to abut against the belt 100. As shown in FIGS. 7 and 8, the displacement part 2 includes a proximal portion 2c having a rod shape and a roller portion 2d.

The roller portion 2d is formed in the distal end of the proximal portion 2c. The proximal portion 2c is made of stainless steel, for example. The roller portion 2d is made of Delrin resin, for example.

The roller portion 2d is a cylindrical rotating body supported by the proximal portion 2a so as to be rotatable independently of the whole rotation of the displacement part 2 to feed the belt 100. As shown in FIGS. 7 and 8, the roller portion 2d rotates when it is caused to abut against the belt 100, and as a result it feeds the belt 100 which is abutting against the roller portion 2d in the feed direction shown by the arrows in FIGS. 7 and 8.

In this embodiment, the elastic body 3 is disposed on one surface of the plate-like member 12, which faces the displacement part 2. The elastic body 3 is disposed so as to be abutted against the proximal portion 2c of the displacement part 2.

The heat flow sensor 4 is disposed on the other surface of the plate-like member 12, which does not face the displacement part 2.

The support mechanism 10 is a mechanism for enabling the case part 9 to rotatably support the displacement part 2. The support mechanism 10 includes a rotation shaft which makes an axis of rotation of the displacement part 2. This rotation shaft is inserted in a through hole formed in the proximal portion 2c of the displacement part 2. In the abnormality estimation apparatus 1 of this embodiment, the distance between the support mechanism 10 and the roller portion 2d is longer than the distance between the support mechanism 10 and a portion of the proximal portion 2c at which the displacement part 2 is caused to abut against the elastic body 3. That is, in this embodiment, the support mechanism 10 makes a fulcrum, the portion of the proximal portion 2c which abuts against the elastic body 3 makes a point of action, and the roller portion 2d makes a point of effort, so that the elastic body 3 is deformed using the principle of leverage.

The radiator 11 is comprised of a heat dissipation fin having a large heat dissipation area for dissipating the heat of the inside of the heat flow sensor 4 and its vicinity to the outside. As shown in FIGS. 7 and 8, the radiator 11 is disposed on the side opposite the elastic body 3 across the heat sensor 4. According to this embodiment, since the radiator 11 is provided, the heat caused by a deformation of the elastic body due to the tension or a change of the tension of the belt 100 can be externally dissipated quickly. Accordingly, since an electromotive force can be brought approximately to zero quickly after a change of the tension of the belt 100 has occurred, the tension of the belt 10 can be measured accurately.

The plate-like member 12 is supported by the case part 9, and supports the elastic body 3 at one surface thereof as shown in FIGS. 7 and 8. The heat flow sensor 4 and the radiator 11 are fixed to the other surface of the plate-like member 12. The plate-like member 12 is made of stainless steel, for example. The plate-like member 12 functions as an intervening part for preventing a force caused by an elastic deformation of the elastic body 3 in accordance with the tension of the belt 100 from affecting the heat flow sensor 4. In this embodiment, since the plate-like member 12 is provided as an intervening part, the heat flow sensor 4 can be prevented from being easily damaged.

The memory stores data representing a relationship between the tension of the belt 100 and the electromotive force to be generated by the heat flow sensor 4 when the case part 9 is placed at a predetermined position.

As described above, according to the abnormality estimation apparatus 1 of this embodiment, the tension or a change of the tension of the belt 100 can be measured like the first embodiment.

Next, the operation of the abnormality estimation apparatus 1 according to this embodiment is explained.

As shown in FIG. 7, the abnormality estimation apparatus 1 is placed at a predetermined position, and the belt 100 is caused to abut against the displacement part 2. At this time, the displacement part 2 rotates with the support mechanism 10 as a fulcrum in accordance with the position of the displacement part 2 and the tension or a change of the tension of the belt 100, causing the elastic body 3 to be compressed to some extent.

When the elastic body 3 is compressed as above, the molecules inside the elastic body 3 are aligned, as a result of which heat is generated inside the elastic body 3. Accordingly, a heat flow heading from the inside of the elastic body 3 to the outside occurs. Since this heat flow passes the front side of the heat flow sensor 4, there occurs a temperature difference between the front side and the back side of the heat flow sensor 4. As a result, an electromotive force occurs as the sensor signal corresponding to the tension of the belt 100, and the abnormality estimation part 7 calculates the tension of the belt 100 based on the sensor signal.

In a case where the tension of the belt 100 increases after the start of measurement, the displacement part 2 rotates downward with the support mechanism 10 as a fulcrum downward in FIG. 8, and as a result, the elastic body 3 is compressed more then than at the start of measurement. The tension of the belt 100 calculated by the abnormality estimation part 7 at this time is larger than that calculated at the time of start of measurement. If the tension of the belt 100 increases beyond a predetermined value, the belt 100 becomes roughly linear in shape.

In a case where the tension of the belt 100 decreases after the start of measurement or after being compressed more after the start of measurement, the displacement part 2 rotates upward in FIG. 8 with the support mechanism 10 as a fulcrum. In this case, the compression of the elastic body 3 is released and the elastic body 3 restores from the elastic deformation, as a result of which cold occurs inside the elastic body 3. As a result, since the temperature of the front side of the heat flow sensor 4 decreases, the temperature difference between the front side and the back side of the heat flow sensor 4 changes from that before the start of measurement. Accordingly, there occurs a change in the electromotive force generated by the feat flow sensor 4. The abnormality estimation part 7 calculates the tension of the belt 100 at this moment that has decreased. The electromotive force generated by the heat flow sensor 4 at this moment is lower than that before the tension of the belt 100 decreases, and is typically a negative value. When the sign of the temperature difference between the front side and the back side of the heat flow sensor 4 changes after the tension of the belt 100 decreases, the sign of the electromotive force also changes.

According to the second embodiment, it is possible to measure the tension or a change of the tension of the belt 100, and performs the abnormality diagnosis for the belt 100 based on the tension or a change or the tension of the belt 100 detected like the first embodiment. Further, since the belt 100 does not directly abut against the heat flow sensor 4, the heat flow sensor 4 is not easily damaged like the first embodiment.

Further, since the plate-like member 12 is provided so as to intervene between the displacement part 2 and the heat flow sensor 4, the heat flow sensor can be further prevented from being damaged.

Further, in the abnormality estimation apparatus 1 of this embodiment, the displacement part 2 is caused to rotate by the tension of the belt 100, and the elastic body 3 is deformed by the rotation of the displacement part 2. That is, in the abnormality estimation apparatus 1 of this embodiment, the tension of the belt 100 is converted to a large force using the principle of leverage. Therefore, since the position of the point of action and the position of the point of effort to the fulcrum can be adjusted, the relationship between the tension of the belt 100 and the displacement of the elastic body 3 or the relationship between the tension of the belt 100 and the electromotive force of the heat flow sensor 4 can be set in a wide range. For example, it is possible to accommodate such a case by increasing the distance between the fulcrum of the displacement part 2 and the point of effort (that is, the roller portion 2d) where the elastic body 3 should be deformed greatly even when the tension of the belt 100 is small.

Third Embodiment

Figure 9:
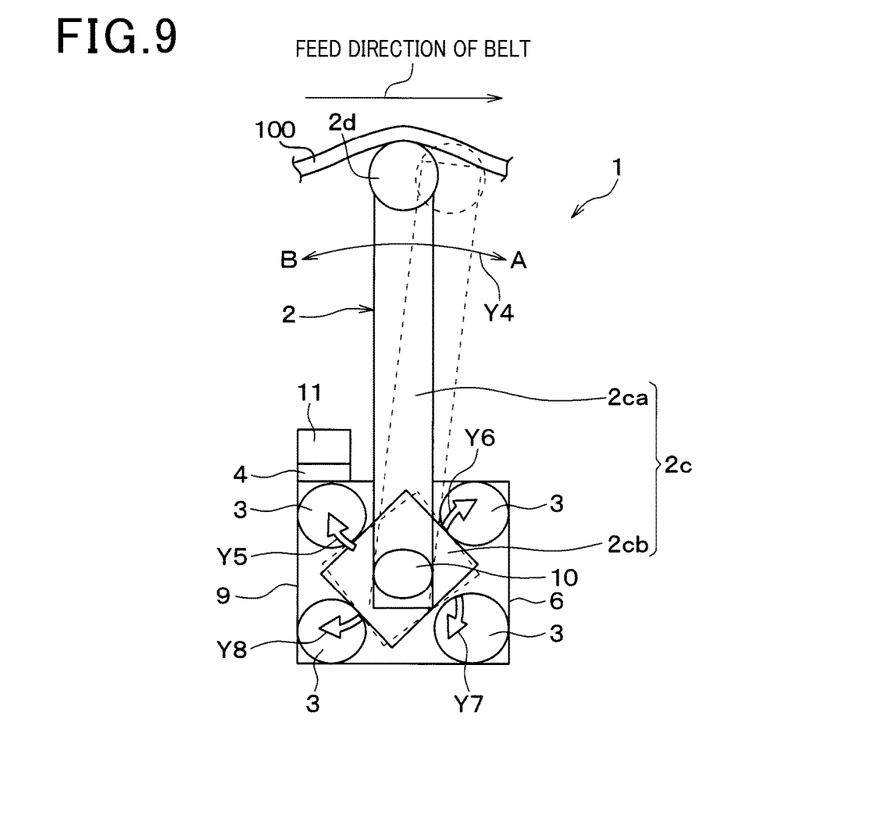
FIG. 9 is a diagram showing the structure of an abnormality estimation apparatus according to a third embodiment of the invention.
Figure 10:
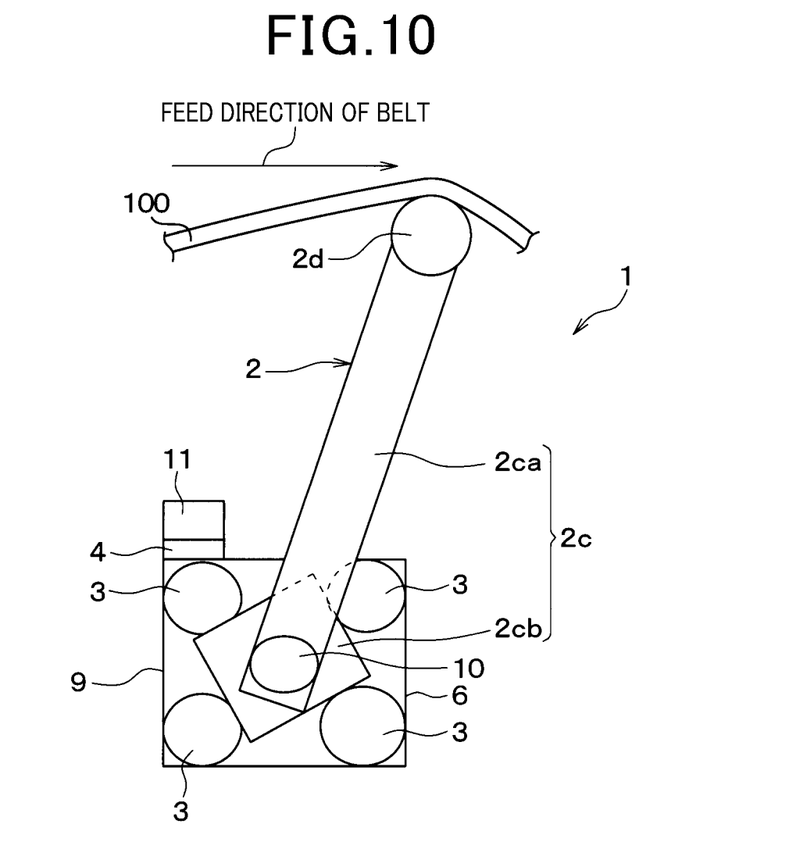
FIG. 10 is another diagram showing the structure of the abnormality estimation apparatus according to the third embodiment of the invention.

Next a third embodiment of the invention is described with a focus on differences with the first embodiment referring to FIGS. 9 and 10.

In FIGS. 9 and 10, the abnormality estimation part 7 and the display part 8 are omitted from illustration. In FIG. 9, the arrow Y4 shows the direction of displacement of the displacement part 2 at a time when the tension of the belt 100 has changed, and the arrows Y5 to Y8 show the directions of displacement of the elastic body 3 at a time when the tension of the belt 100 has increased.

In this embodiment, the displacement part 2 includes the proximal portion 2c and the roller portion 2d. As shown in FIGS. 9 and 10, the proximal portion 2c of the displacement part 2 includes a rod-shaped portion 2ca formed with the roller portion 2d at one distal end thereof and formed with a polyhedral portion 2cb at the other distal end thereof. In this embodiment, the polyhedral portion 2cb of the displacement part 2 has a cubic shape. The rod-shaped portion 2ca and the polyhedral portion 2cb of the displacement part 2 rotate together with the support mechanism 10 as a fulcrum. The rod-shaped portion 2ca of the displacement part 2 is made of stainless steel, for example. The roller portion 2d is made of Delrin resin, for example. The polyhedral portion 2cb of the displacement part 2 is made of stainless steel, for example.

As shown in FIGS. 9 and 10, the elastic body 3 is disposed at a plurality of positions around the polyhedral portion 2cb in this embodiment. The elastic bodies 3 are housed in the case part 9. Each of the plurality of the elastic bodies 3 faces an opposite one of a plurality of the surfaces of the polyhedral portion 2cb. That is, the elastic bodies 3 are disposed such that each one of them abuts a corresponding one of the surfaces of the polyhedral portion 2cb and is deformed when the polyhedral portion 2cb rotates. In this embodiment, the elastic bodies 3 are four spherical elastic bodies. When the polyhedral portion 2cb of the displacement part 2 rotates with the support mechanism 10 as a fulcrum, the four spherical elastic bodies are compressed by the displacement of the surfaces of the polyhedral portion 2cb due to the rotation.

In the third embodiment, the plate-like member 12 is removed. The case part 9 functions as the intervening part that prevents a force caused by an elastic deformation of the elastic body due to the tension of the belt 100 from affecting the heat flow sensor 4.

Next, the operation of the abnormality estimation apparatus 1 according to the third embodiment is explained.

As shown in FIGS. 9 and 10, the abnormality estimation apparatus 1 is placed at a predetermined position, and the belt 100 is caused to abut against the displacement part 2. At this time, the displacement part 2 is in a state of being caused to abut against the elastic body 3 so as to slightly compress the elastic body 3.

In this state, since the elastic body 3 is only slightly compressed, the electromotive force generated in the heat flow sensor 4 at this moment (that is, at the start of measurement) is approximately zero.

In a case where the tension of the belt 100 increases thereafter, the displacement part 2 rotates in the direction A or B with the support mechanism 10 as a fulcrum. Here, it is assumed that the displacement part 2 rotates in the direction A. The elastic body 3 is compressed more then than at the start of measurement. In this case, there occurs an electromotive force in accordance with the degree of a change of the tension of the belt 100. The abnormality estimation part 7 calculates the tension of the belt 100 at this moment that has increased. If the tension of the belt 100 increases beyond a predetermined value, the belt 100 becomes roughly linear in shape.

In a case where the tension of the belt 100 decreases after the start of measurement or after being compressed more after the start of measurement, the displacement part 2 rotates in the direction B in FIG. 9 with the support mechanism 10 as a fulcrum. In this case, the compression of the elastic body 3 is released and the elastic body 3 restores from the elastic deformation, as a result of which cold occurs inside the elastic body 3. As a result, since the temperature of the front side of the heat flow sensor 4 decreases, the temperature difference between the front side and the back side of the heat flow sensor 4 changes from that before the decrease of the tension of the belt 100. Accordingly, there occurs a change in the electromotive force generated by the feat flow sensor 4. The tension calculation part 7 calculates the tension of the belt 100 at this moment that has decreased. When the sign of the temperature difference between the front side and the back side of the heat flow sensor 4 changes after the tension of the belt 100 decreases, the sign of the electromotive force also changes.

According to the third embodiment, it is possible to measure the tension or a change of the tension of the belt 100, and performs the abnormality diagnosis for the belt 100 based on the tension or a change or the tension of the belt 100 detected like the second embodiment. Further, since the belt 100 does not directly abut against the heat flow sensor 4, the heat flow sensor 4 is not easily damaged like the second embodiment.

Further, since the elastic bodies 3 can be deformed efficiently using the respective surfaces of the polyhedral portion 2cb, it is possible to increase the electromotive force of the heat flow rate sensor 4 efficiently.

Fourth Embodiment

Figure 11:
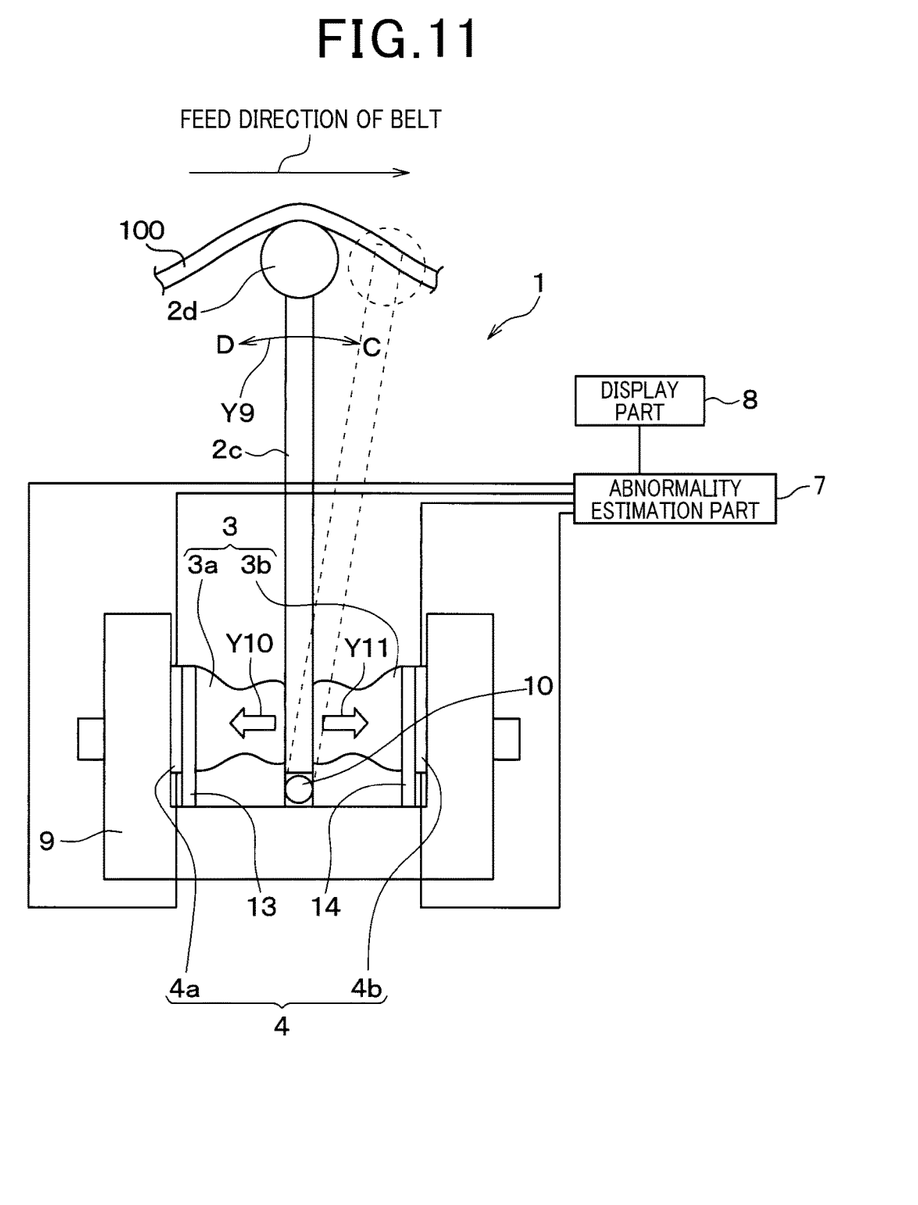
FIG. 11 is a diagram showing the structure of an abnormality estimation apparatus according to a fourth embodiment of the invention.
Figure 12:
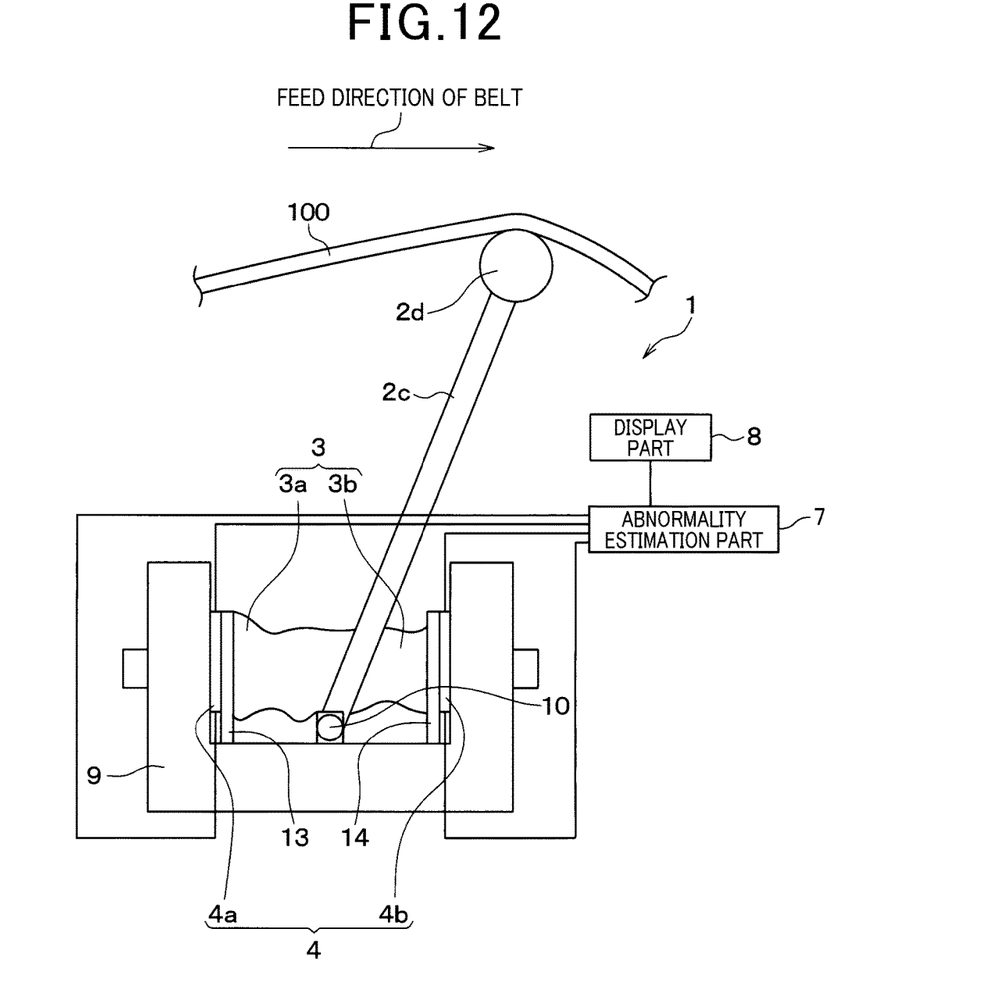
FIG. 12 is another diagram showing the structure of the abnormality estimation apparatus according to the fourth embodiment of the invention.

Next a fourth embodiment of the invention is described with a focus on differences with the first embodiment referring to FIGS. 11 and 12.

In FIGS. 11 and 12, the abnormality estimation part 7 and the display part 8 are omitted from illustration. In FIG. 11, the arrow Y9 shows the direction of displacement of the displacement part 2 at a time when the tension of the belt 100 has changed, the arrow Y10 shows the direction of displacement of the elastic body 3 at a time when the tension of the belt 100 has increased causing the displacement part 2 to displace in the direction shown by the arrow D, and the arrow Y11 shows the direction of displacement of the elastic body 3 at a time when the tension of the belt 100 has increased causing the displacement part 2 to be displaced in the direction shown by the arrow C.

As shown in FIGS. 11 and 12, the elastic body 3 includes a first part 3a and a second part 3b in this embodiment. The first part 3a is disposed on the side of one direction (direction C) of the rotation of the displacement part 2. The second part 3a is disposed on the side of the other direction (direction D) of the rotation of the displacement part 2.

As shown in FIGS. 11 and 12, in this embodiment, the plate-like member 12 is removed, and instead, plate-like members 13 and 14 are provided. The plate-like members 13 and 14 are fixed to the case part 9.

The first part 3a of the elastic body 3 is disposed between the plate-like member 13 and the proximal portion 2c of the displacement part 2 so as to be compressed therebetween. The second part 3b of the elastic body 3 is disposed between the plate-like member 14 and the proximal portion 2c of the displacement part 2 so as to be compressed therebetween.

In this embodiment, the heat flow sensor 4 is comprised of a first detection part 4a for detecting mainly a heat flow caused by an elastic deformation of the first part 3a of the elastic body 3, and a second detection part 4b for detecting mainly a heat flow caused by an elastic deformation of the second part 3b of the elastic body 3. Each of the first and second detection parts 4a and 4b is the same in structure as the heat flow sensor 4 described in the first embodiment. The first detection part 4a is configured to generate a positive electromotive force when a heat flow passes from the front side to the back side of the first detection part 4a. The second detection part 4b is configured to generate a positive electromotive force when a heat flow passes from the front side to the back side of the second detection part 4b.

As shown in FIGS. 11 and 12, the first detection part 4a of the heat flow sensor 4 is disposed opposite to the elastic body 3 across the plate-like member 13. Likewise, the second detection part 4a of the heat flow sensor 4 is disposed opposite to the elastic body 3 across the plate-like member 14. The first and second detection parts 4a and 4b of the heat flow sensor 4 are electrically connected to the abnormality estimation part 7. The first detection part 4a generates an electromotive force in accordance with a deformation amount of the first part 3a of the elastic body 3 when a heat flow has occurred in the first part 3a of the elastic body 3. The second detection part 4b generates an electromotive force in accordance with a deformation amount of the second part 3b of the elastic body 3 when a heat flow has occurred in the second part 3b of the elastic body 3.

The plate-like member 13 functions as an intervening part that prevents a force caused by an elastic deformation of the first part 3a of the elastic body 3 due to the tension of the belt 100 from affecting the first detection part 4a of the heat flow sensor 4. The plate-like member 14 functions as an intervening part that prevents a force caused by an elastic deformation of the second part 3b of the elastic body 3 due to the tension of the belt 100 from affecting the second detection part 4b of the heat flow sensor 4. The provision of the plate-like members 13 and 14 provides an advantage that the heat flow sensor 4 is not easily damaged.

In this embodiment, the abnormality estimation part 7 calculates the tension or a change of the tension of the belt 100 based on the electromotive force detected by the first detection part 4a and the electromotive force detected by the second detection part 4b of the heat flow sensor 4. More specifically, the abnormality estimation part 7 calculates the tension or a change of the tension of the belt 100 based on the difference between the electromotive force detected by the first detection part 4a and the electromotive force detected by the second detection part 4b of the heat flow sensor 4.

Next, the operation of the abnormality estimation apparatus 1 according to the fourth embodiment is explained.

As shown in FIGS. 11 and 12, the abnormality estimation apparatus 1 is placed at a predetermined position, and the belt 100 is caused to abut against the displacement part 2. At this time, the abnormality estimation apparatus 1 is in a state to start measurement where the displacement part 2 of the tension measuring apparatus 1 compresses the first part 3a and the second part 3b to some extent while it is caused to abut against the elastic body 3.

In this embodiment, the abnormality estimation apparatus 1 is left in this measurement starting state for a predetermined time so that the heat generated inside the elastic body 3 due to the compression of the elastic body 3 is sufficiently dissipated to the outside. Accordingly, in this state, the electromotive force of the heat flow sensor 4 becomes approximately zero.

In a case where the tension of the belt 100 increases thereafter, the displacement part 2 rotates in the direction C in FIG. 11 with the support mechanism 10 as a fulcrum as shown in FIG. 12. The second part 3b of the elastic body 3 is compressed in this state more than in the measurement starting state, while the first part 3a of the elastic body 3 is released from the compression to restore it from being deformed. As a result, heat occurs in the second part 3b of the elastic body 3, while cold occurs in the first part 3a of the elastic body 3. Accordingly, a positive electromotive force occurs in the first detection part 4a of the heat flow sensor 4, while a negative electromotive force occurs in the second detection part 4b of the heat flow sensor 4. In this embodiment, the abnormality estimation part 7 calculates the tension or a change of the tension of the belt 100 based on the difference between the electromotive force detected by the first detection part 4a and the electromotive force detected by the second detection part 4b of the heat flow sensor 4. Accordingly, the value of a change of the tension of the belt 100 calculated at this moment by the abnormality estimation part 7 is larger than that calculated at the start of measurement. When heat due to compression remains in the elastic body 3 or when the elastic body 3 has heat due to circumferential heat, a positive electromotive force may occur also in the second detection part 4b of the heat flow sensor 4.

According to this embodiment, since the tension or a change of the tension of the belt 100 is calculated based on the difference between the electromotive forces of the two heat flow sensors (the first and second detection parts 4a and 4b), an advantage that the output of the abnormality estimation part 7 can be increased is obtained.

In a case where the tension of the belt 100 decreases after the state shown in FIG. 12, the displacement part 2 rotates in the direction D in FIG. 11 with the support mechanism 10 as a fulcrum to return to the state of starting measurement. In this case, the second part 3b of the elastic body 3 is released from the compression to restore from being deformed. Therefore, since cold occurs inside the second part 3b of the elastic body 3, the electromotive force occurring in the second detection part 4b of the heat flow sensor 4 decreases. On the other hand, since the first part 3a of the elastic body 3 is compressed, heat occurs inside the first part 3a of the elastic body 3. As a result, the difference in electromotive force between the first detection part 4a and the second detection part 4b decreases, typically to a negative value. Accordingly, it is detected as a decrease of the tension of a belt 100 by the abnormality estimation part 7.

According to the fourth embodiment, it is possible to measure the tension or a change of the tension of the belt 100, and performs the abnormality diagnosis for the belt 100 based on the tension or a change or the tension of the belt 100 detected like the second embodiment.

According to the tension measuring apparatus 1 according to this embodiment, since the plate-like member 14 is provided, the heat flow sensor 4 is not easily damaged like the second embodiment.

The tension measuring apparatus 1 according to this embodiment provides the advantage that the relationship between the tension of the belt 100 and the displacement of the elastic body 3 or the relationship between the tension of the belt 100 and the electromotive force of the heat flow sensor 4 can be set in a wide range like the second embodiment.

In this embodiment, the tension or a change of the tension of the belt 100 is calculated based on the electromotive force detected by the first detection part 4a and the electromotive force detected by the second detection part 4b of the heat flow sensor 4. Accordingly, the advantage that the output of the abnormality estimation part 7 can be increased is obtained. The output of the tension calculation part 7 in this embodiment is approximately twice as that in the case of using a single heat flow sensor.

In this embodiment, the tension calculation part 7 calculates the tension or a change of the tension of the belt 100 based on the electromotive force detected by the first detection part 4a and the electromotive force detected by the second detection part 4b of the heat flow sensor 4. Accordingly, since temperature drifts included in the two electromotive forces cancel with each other, it is possible to prevent the temperature drifts from affecting the output. That is, in the case where only the single heat flow sensor 4 is provided, it is not possible to determine, when an electromotive force of the heat flow sensor 4 has increased, whether it is due to an increase of the tension of the belt 100 causing the elastic body 3 to be deformed, or it is due to an increase of the circumferential temperature. On the other hand, in the case where two heat flow sensors (the first and second detection parts 4a and 4b) are provided, since the tension or a change of the tension of the belt 100 is calculated based on the difference between the two electromotive forces of the two heat flow sensors, it is possible to determine that the elastic body 3 has been deformed due to an increase of the tension of the belt 100 removing the effect of a change of the circumferential temperature. Specifically, in this embodiment, the heat flow sensor 4 is configured to generate a positive electromotive force when a heat flow passes from the front side to the back side thereof, and the tension or a change of the tension of the belt 100 is calculated based on the difference in electromotive force between the first and second detection parts 4a and 4b as two heat flow sensors.

According to this embodiment, it is possible to remove the effect of the temperature drifts caused by heat flows passing from the front side to the back side of each of the first and second detection parts 4a and 4b.

Incidentally, the effect of the temperature drift caused by a heat flow passing from the back side to the front side of the first detection part 4a and a heat flow passing from the front side to the back side of the second detection part 4b can be removed by calculating the tension or a change of the tension of the belt 100 based on the sum of the electromotive forces of the two heat flow sensors (the first and second detection parts 4a and 4b), or by causing the second detection part 4b to generate a positive electromotive force when a heat flow passes from the front side to the back side of the second detection part 4b.

Other Embodiments

It is a matter of course that various modifications can be made to the above described embodiments as described below.

Figure 13:
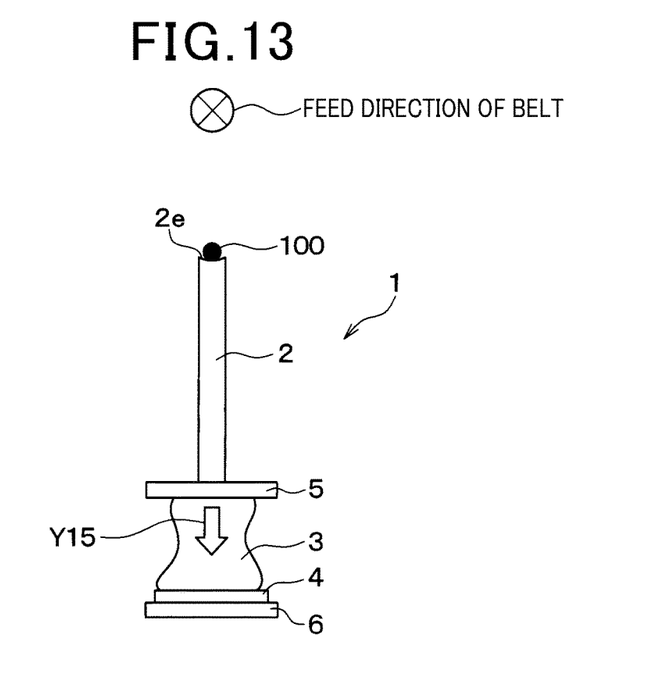
FIG. 13 is a diagram showing the structure of an abnormality estimation apparatus according to a variant embodiment of the invention.
Figure 14:
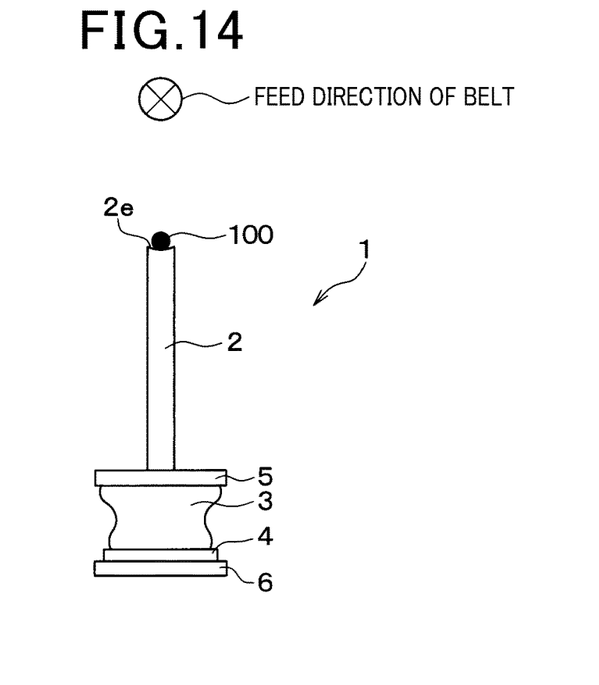
FIG. 14 is another diagram showing the structure of the abnormality estimation apparatus according to the variant embodiment of the invention.

In the first to fourth embodiments, the displacement part 2 includes the roller portion 2b or 2d to feed the belt 100. However, the roller portion 2b or 2d may not be provided if the belt 100 is fed by causing the belt 100 to abut against the displacement part 2. That is, as shown in FIGS. 13 and 14, the belt 100 may be fed by causing the belt 100 to abut against a surface 2e of the displacement part 2. In this case, it is preferable that the coefficient of friction of the surface 2e is small so that the belt 100 abutting against the surface 2e can easily slide thereon. In FIGS. 13 and 14, the abnormality estimation part 7 and the display part 8 are omitted from illustration. The arrow Y15 in FIG. 13 shows the direction of deformation of the elastic body 3 when the tension of the belt 100 has increased.

The above explained preferred embodiments are exemplary of the invention of the present application which is described solely by the claims appended below. It should be understood that modifications of the preferred embodiments may be made as would occur to one of skill in the art.

What is claimed is:

1. An abnormality estimation apparatus for estimating an abnormality in a belt of a belt conveyor, comprising:
   a displacement part that is displaced in accordance with tension or a change of the tension of the belt when the displacement part is caused to abut against the belt to receive the tension of the belt;
   an elastic body that is elastically deformed in accordance with displacement of the displacement part;
   a heat flow sensor that detects a heat flow occurring due to elastic deformation of the elastic body;
   a heat conducting member disposed adjacently to the heat flow sensor; and
   an abnormality estimation part that estimates whether there is an abnormality in the belt based on a detection result by the heat flow sensor, wherein
   the heat flow sensor is disposed between the elastic body and the heat conducting member.

2. The abnormality estimation apparatus according to claim 1, further comprising a case part that supports the elastic body and a support mechanism that causes the case part to rotatably support the displacement part, wherein
   the displacement part rotates with the support mechanism as a fulcrum, and the elastic body is elastically deformed in accordance with displacement of the displacement part due to rotation of the displacement part with the support mechanism as the fulcrum.

3. The abnormality estimation apparatus according to claim 2, wherein
   the elastic body includes a first part and a second part,
   the displacement part compresses the second part and restores the first part from being compressed when the displacement part rotates in a first direction, and restores the second part from being compressed and compresses the first part when the displacement part rotates in a second direction opposite the first direction,
   the heat flow sensor includes a first detection part for detecting a first heat flow caused by elastic deformation of the first part and a second detection part for detecting a second heat flow caused by elastic deformation of the second part, and
   the abnormality estimation part calculates the tension of the belt based on an electromotive force occurring in the first part depending on the first heat flow and an electromotive force occurring in the second part depending on the second heat flow.

4. The abnormality estimation apparatus according to claim 2, wherein the displacement part rotates to feed the belt when the displacement part is caused to abut against the belt.

5. The abnormality estimation apparatus according to claim 1, further comprising an intervening part that intervenes between the displacement part and the heat flow sensor to prevent a force caused by elastic deformation of the elastic body in accordance with the tension of the belt from affecting the heat flow sensor.

* * * * *